United States Patent [19]

Welsh

[11] Patent Number: 4,730,483

[45] Date of Patent: Mar. 15, 1988

[54] MEANS FOR DETERMINING MAXIMUM IRONING REDUCTION

[75] Inventor: Robert E. Welsh, Mount Lebanon, Pa.

[73] Assignee: Aluminum Company of America, Pittsburgh, Pa.

[21] Appl. No.: 839,782

[22] Filed: Mar. 14, 1986

[51] Int. Cl.$^4$ .............................................. G01N 3/28
[52] U.S. Cl. .......................................... 73/87; 73/835; 73/10
[58] Field of Search ................ 72/3, 4, 347, 348, 276, 72/283, 284; 73/826, 834, 835, 9, 10, 64, 762, 783, 87, 799, 821

[56] References Cited

U.S. PATENT DOCUMENTS

| Re. 14,421 | 1/1918 | Erichsen | 73/87 |
|---|---|---|---|
| 1,653,714 | 12/1927 | Lewis et al. | 73/87 |
| 2,262,084 | 11/1941 | Alexander | 73/87 |
| 2,369,187 | 2/1945 | Swertfager et al. | 72/345 |
| 2,875,608 | 3/1959 | Engelhardt et al. | 73/87 |
| 3,139,749 | 7/1964 | Zaat | 73/87 |
| 4,075,886 | 2/1978 | Barker | 73/826 |
| 4,129,024 | 12/1978 | Deveney | 72/347 |

FOREIGN PATENT DOCUMENTS

| 579625 | 7/1958 | Italy | 72/347 |
|---|---|---|---|
| 11431 | 5/1969 | Japan | 73/87 |
| 128770 | 7/1950 | Sweden | 73/87 |
| 595031 | 2/1978 | U.S.S.R. | 72/283 |
| 979952 | 12/1982 | U.S.S.R. | 73/783 |

OTHER PUBLICATIONS

Metalworking Lubricants by E. L. H. Bastian, McGraw-Hill Book Co., Inc., (1951), pp. 323-334.
The Making, Shaping and Treating of Steel by United States Steel; © 1957, 7th ed., pp. 923 and 924.

Primary Examiner—Lowell A. Larson
Attorney, Agent, or Firm—Elroy Strickland

[57] ABSTRACT

Apparatus and method for determining the fracture resistance of thin wall hollow articles when ironed, the method including the step of providing a drawing die and punch or a mandrel having a portion thereof tapered in a continuous, linear manner. The taper is such that it provides a continuous decrease in punch-to-die clearance when the two are moved together, and thus a continuous range of ironing reductions along the side wall of an article located between the punch and die. The taper of the punch begins adjacent the forward end thereof and is sized to effect conventional thinning of the side wall of the article at the onset of ironing. The final diameter of the taper of the punch, however, is such that fracturing of the side wall is assured in the ironing process.

5 Claims, 1 Drawing Figure

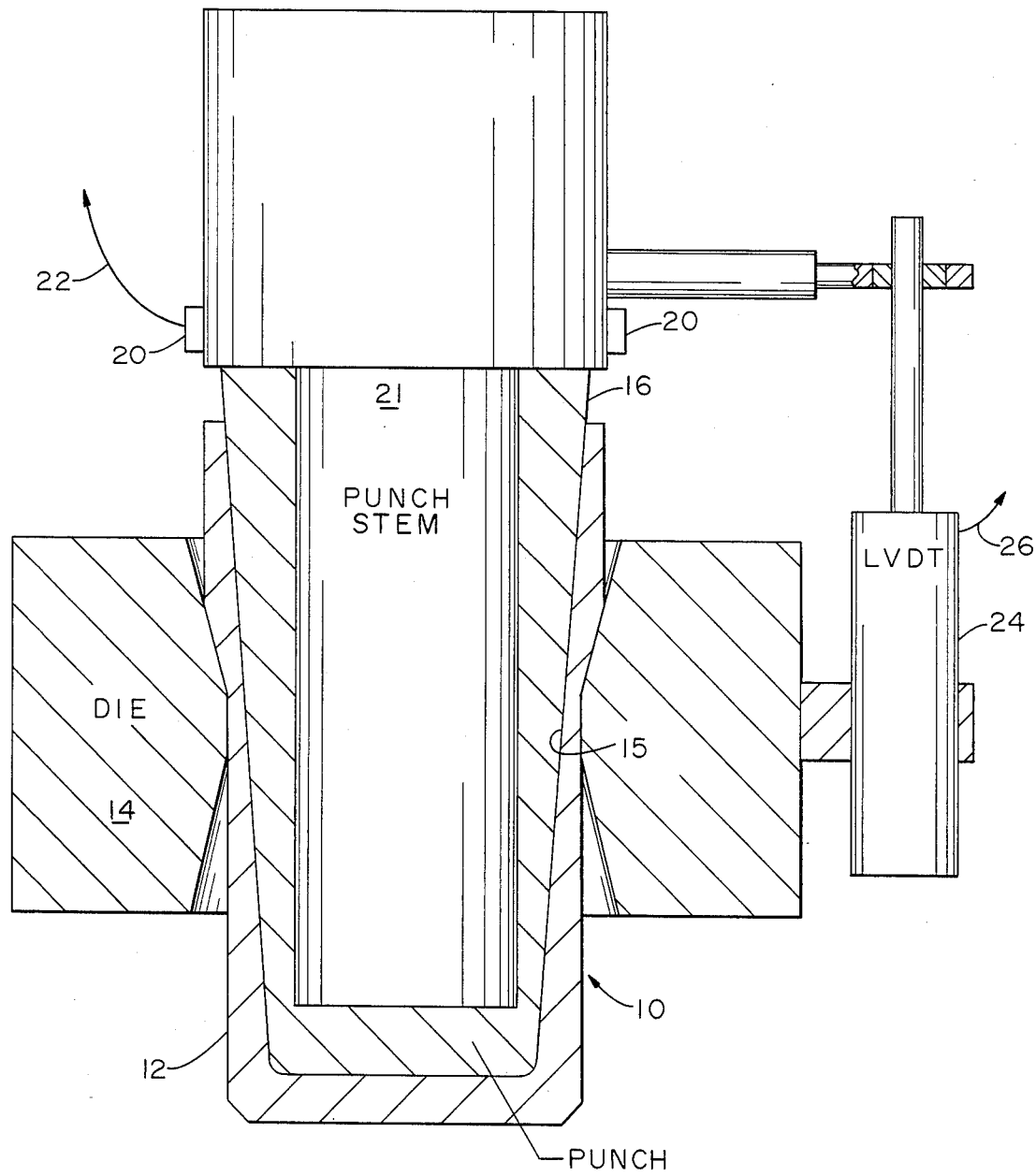

MEANS FOR DETERMINING MAXIMUM IRONING REDUCTION

The present invention relates generally to a punch and die arrangement for gradually thinning the side wall of a deepdrawn article until the wall fractures in tension.

Typically, in determining the maximum reduction in wall thickness of a hollow article comprised of a particular ductile alloy, or in determining the lubricating capability of a particular formulation of a process lubricant, or evaluating the performance of an ironing die profile, ironing dies of progressively smaller inner diameters are employed to iron the walls of a plurality (usually thousands) of hollow articles until the frequency of fracture reaches an unacceptably high level. As can be appreciated, such a process requires a plurality of dies, as well as the use of a number of hollow articles until the limiting ironing reduction using the alloy, lubricant, or die profile is determined. The frequent replacement of dies allows inconsistency in die alignment, die profile geometry, and die surface condition, introducing increased variance into test results and reducing the discriminating power of the test. The use of multiple tests, i.e., multiple dies and multiple articles, is also time consuming and therefore economically costly.

BRIEF SUMMARY OF THE INVENTION

The method and means of the present invention is directed to the use of a single tapered punch or mandrel, and a single outer ironing die to gradually iron the side wall of a single article made of a particular alloy under test and/or the use of a particular drawing lubricant and/or the use of a particular ironing die profile for the ironing process. The outer diameter of the punch increases linearly from the leading end (nose) of the punch to the trailing end (base), such that a continuous increase in reduction along each test article's side wall is effected by drawing the article, mounted on the punch, through the die. The diameter nearer the nose of the punch is chosen in conjunction with the inner diameter of the single ironing die to provide a conventional reduction in side wall thickness and thus ensure against a ductile fracture in the side wall at this location. The punch diameter at the base is chosen, dependent on the inner diameter of the die, to ensure fracture in the tapered region of the side wall. The fracture event is detected by a major, abrupt drop in the load exerted at the punch base to draw the article through the die, while the amount of reduction is determined from the relative displacement of the punch and die. The punch load and displacement can be computermonitored and analyzed to provide an accurate representation of the event at high punch speeds.

BRIEF DESCRIPTION OF THE DRAWING

The invention, along with its advantages and objectives, will be best understood from consideration of the following detailed description and the accompanying drawing in which the sole FIGURE thereof shows, inter alia, an assembly, in cross section, of an ironing die and a tapered punch or mandrel employed for the purposes of the invention.

PREFERRED EMBODIMENT OF THE INVENTION

Referring now to the drawing and figure, a draw punch and die arrangement 10 is depicted in vertical section and in combination with a hollow cylindrical container 12. The die of the arrangement, indicated by numeral 14, has a circular opening 15 while the punch or mandrel can be a solid or hollow circular structure (in cross section), indicated in the drawing by numeral 16. Die 14 can be a conventional ironing die, in combination with a tapered punch, described in detail below, for ironing the side wall 18 of container 12. The container can be made from an original cup (not shown), the cup itself being deep-drawn by the tapered punch, through a radiused profile of the die to a diameter equal to the tapered punch. (Prior to this, an initial deep-draw in a separate cupping press, forming the cup from a flat circular blank of metal to a final diameter greater than the ironing punch nose, may be required, depending on the formability of the test material and the total deep-draw reduction required). The cup wall usually has a thickness nonuniformity resulting from the effects of planar anisotropy in deep-drawing. This may be prevented by a small wall thickness reduction (ironing reduction) accomplished during the deep-draw process by using a draw die having inner diameter that provides a punch-die clearance less than the cup wall thickness that would otherwise result. When the tapered punch is used with the proper deep-draw die inner diameter, this results in a tapered cup side wall without causing a fracture.

The punch or mandrel 16 of the invention is specifically designed and made with a slight taper (on the order of 0.01 to 10 degrees), the diameter of the punch increasing from the nose or forward end thereof to a base location remote from the nose end. (In the figure, the amount of taper is exaggerated for purposes of illustration).

The amount of the taper of 16 provides a continuous reduction in the thickness of the side wall of a hollow article, such as wall 18 of metal container 12, as the punch axially moves through the die opening, in a manner that permits a single continuous stroke of a press (not shown), operable to relatively move the punch and die, until the reduction is completed; the reduction is completed when a ductile fracture occurs in the side wall. In this manner, the invention provides a quick quantitative result from each article tested which is descriptive of, for example, the particular alloy's forming performance in ironing. This technique eliminates the need for many tests at different reductions, which can only provide an upper or lower boundary on maximum reduction of each article, based on success or failure at a chosen reduction. In addition, greater test condition consistency, i.e., die alignment, die profile, die surface condition, and punch-to-die concentricity, is maintained by eliminating the need to use different dies and replace them in the press to incrementally change ironing reduction.

The precise occurrence of the fracture, indicating attainment of maximum ironing reduction, can be determined by the use of strain gauges 20 suitably attached to the outside surface of the punch stem, as shown in the figure. A suitable strain gauge consists of a small diameter, continuous wire disposed in a planar configuration of many straight, parallel segments aligned with the direction of loading. The material (punch stem) strain is determined from the identical elongation of the wire of the gauge, which results in, and is detected as, a change in voltage caused by a change in the wire's electrical resistance. Exitation voltage is required for operation of each of the gauges, and subsequent amplification and filtering of the output signals received from the gauges via a common lead 22, is accomplished by a separate electronic signal conditioning device (not shown). When a ductile fracture occurs in the side wall of article 12, the load, i.e., strain, on the gauges is abruptly reduced such that the gauges' electrical resistances are abruptly changed. The occurrence of fracture can thus be detected by a computer equipped with an analog-to-digital converter to monitor the output voltage signals of the strain gauges after amplification and filtering by the electronic signal conditioning device. The computer can permanently store this data for later use in analyzing the ability of the material of the article 12 being ironed to undergo high reductions.

This analysis of maximum reduction can be made by observing the position of punch 16 relatively to die 14, and thus the location of the fracture in wall 18. The fracture occurs some length from the punch nose at some relative position of die 14 and punch 16. If electrical instrumentation, such as a computer, is employed to detect and record the location of the fracture, a position sensor 24, such as a linear variable differential transformer (LVDT) can be used in the manner shown in the drawing. As depicted schematically in the figure, the transformer device is mounted between the punch and die, such that the ferromagnetic core of the device is moved relative to the transformer windings of the device, suitably housed. The output 26 of device 24 is also connected to the analog-to-digital converted of the computer for monitoring the relative motion of punch and die with time. By knowing the occurrence of fracture (from gauges 20) and the relative motion of punch to die (from LVDT 24), the computer, with proper programming, can readily determine location of fracture relative to the punch nose and, from the known punch taper and die inner diameter, the final thickness of the side wall at fracture. If the article side wall has previously been sized, the initial wall thickness at the fracture (immediately before the ironing die) can similarly be determined; otherwise, the thickness may be measured by micrometers after removal of the unironed segment of the article from the press. From initial and final side wall thickness at fracture, a precise measure of maximum ironing reduction is quickly obtained for each article for known and controllable lubrication, die profile, and other test conditions.

While the invention has been described in terms of preferred embodiments, the claims appended hereto are intended to encompass all embodiments which fall within the spirit of the invention.

What is claimed is:

1. Apparatus for testing cylindrical, hollow articles for forming limits when side walls of the articles are ironed using a single press stroke on a single cylindrical, hollow article, said means comprising:

an ironing die, a punch or mandrel having a linearly tapered portion for entering said die and thereby providing a continuous decrease in punch-to-die clearance and thus a continuous range of ironing reductions along the side wall of an article located between the punch and die, the tapered portion having an initial outside diameter providing a die clearance that effects non-critical thinning of the side wall of the article at the onset of ironing to ensure against premature fracturing of the side wall, while the final outside diameter of the punch provides a punch-to-die clearance such that fracturing of the side wall occurs, and means to determine final thickness of the fractured side wall.

2. The apparatus of claim 1 in which the means to determine final wall thickness includes a sensing device located to detect the occurrence of fracturing.

3. The apparatus of claim 2 in which the sensing device is a strain gauge.

4. The apparatus of claim 1 in which the means to determine final wall thickness includes a device for detecting relative position of the die and punch.

5. A method of determining forming limits in ironing the side wall of cylindrical, hollow articles, comprising the steps of:

providing an ironing die, providing a punch or mandrel having a portion tapered in a continuous, linear manner from a location adjacent the nose end of the punch to a location remote from the nose end, thereby providing a continuous range of punch-to-die clearances and ironing reductions, placing a cylindrical article between the die and punch mandrel, relatively moving the die and punch to iron the side wall of the article until punch-to-die clearance is such that the fracture of the side wall occurs, and determining the thickness of the fractured side wall.

* * * * *